United States Patent [19]

Feher

[11] Patent Number: 4,777,802
[45] Date of Patent: Oct. 18, 1988

[54] BLANKET ASSEMBLY AND SELECTIVELY ADJUSTABLE APPARATUS FOR PROVIDING HEATED OR COOLED AIR THERETO

[76] Inventor: Steve Feher, 1909 Aleo Pl., Honolulu, Hi. 56822

[21] Appl. No.: 41,414

[22] Filed: Apr. 23, 1987

[51] Int. Cl.$^4$ .................................... F25B 21/02
[52] U.S. Cl. ................................. 62/3; 62/261; 5/482
[58] Field of Search ............... 62/3, 261; 128/400, 128/402; 98/1; 5/482, 486

[56] References Cited

U.S. PATENT DOCUMENTS

| | | | |
|---|---|---|---|
| 2,991,627 | 7/1961 | Suits | 62/3 |
| 3,080,723 | 3/1963 | Price | 62/3 |
| 3,099,137 | 7/1963 | Jamison | 62/3 |
| 3,136,577 | 6/1964 | Richard | 62/3 X |
| 3,154,926 | 11/1964 | Hirschhorn | 62/3 |
| 4,132,262 | 1/1979 | Wibell | 62/261 X |
| 4,660,388 | 4/1987 | Greene, Jr. | 62/261 |

Primary Examiner—Lloyd L. King
Attorney, Agent, or Firm—George J. Netter

[57] ABSTRACT

A blanket assembly has an outer layer constructed of a relatively close weave fabric preventing air flow therethrough. Underneath the top layer is a second layer of material edge connected to the top layer and which is constructed of a material permeable to air, such as relatively thin taffeta, for example. A cavity exists between the two layers which receives pressurized cooled or heated air that passes through the air permeable layer to cool or heat the individual using the blanket assembly. A modified blanket assembly construction includes rigid edge wall members holding the outer and inner layers separated at a predetermined spacing reducing "pinch-off" between the layers restricting air flow within parts of the cavity or chamber. Peltier effect elements are selectively energizable to heat or cool air provided to the blanket assembly cavity.

20 Claims, 10 Drawing Sheets

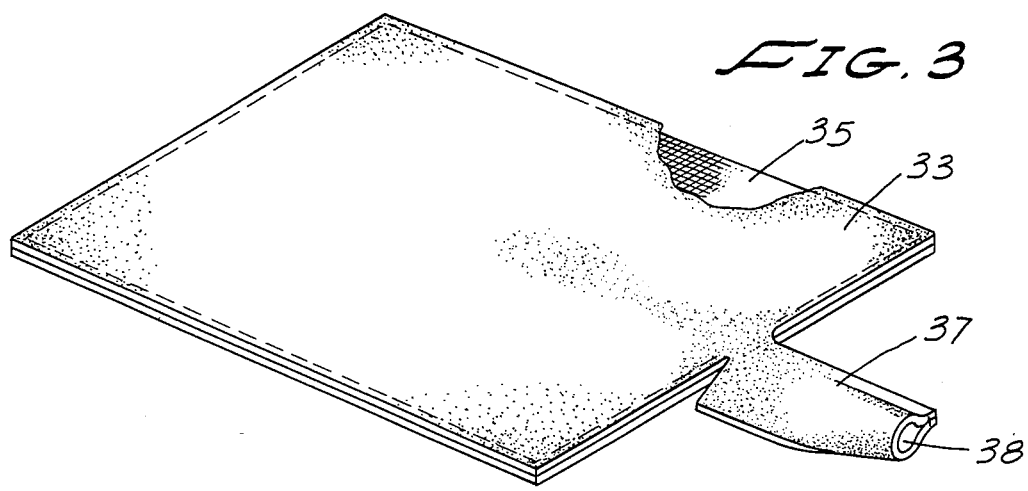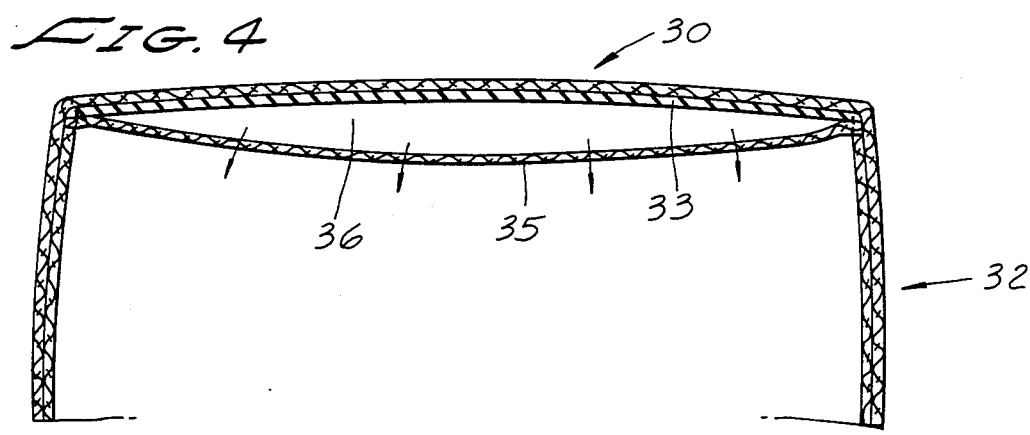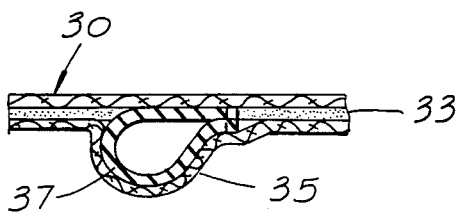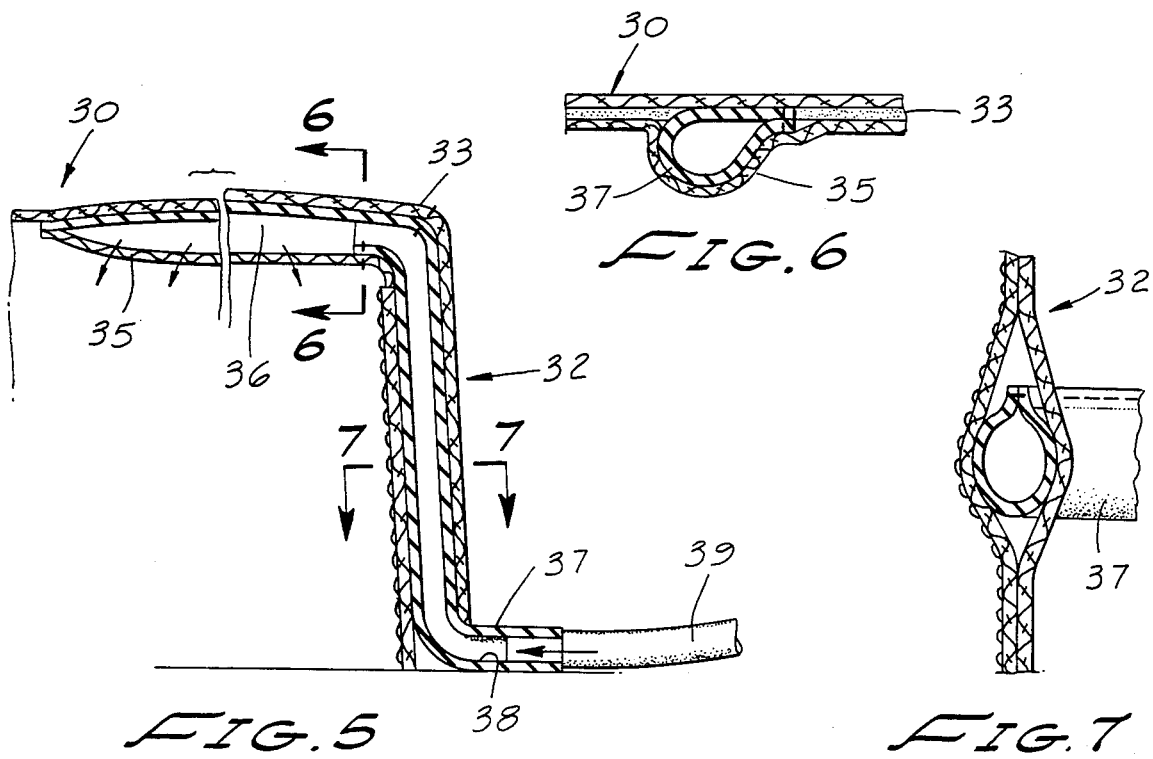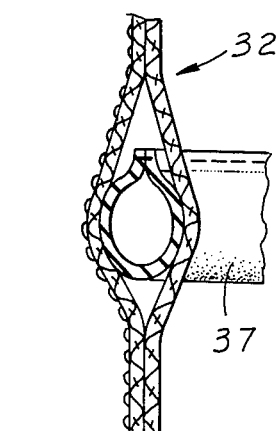

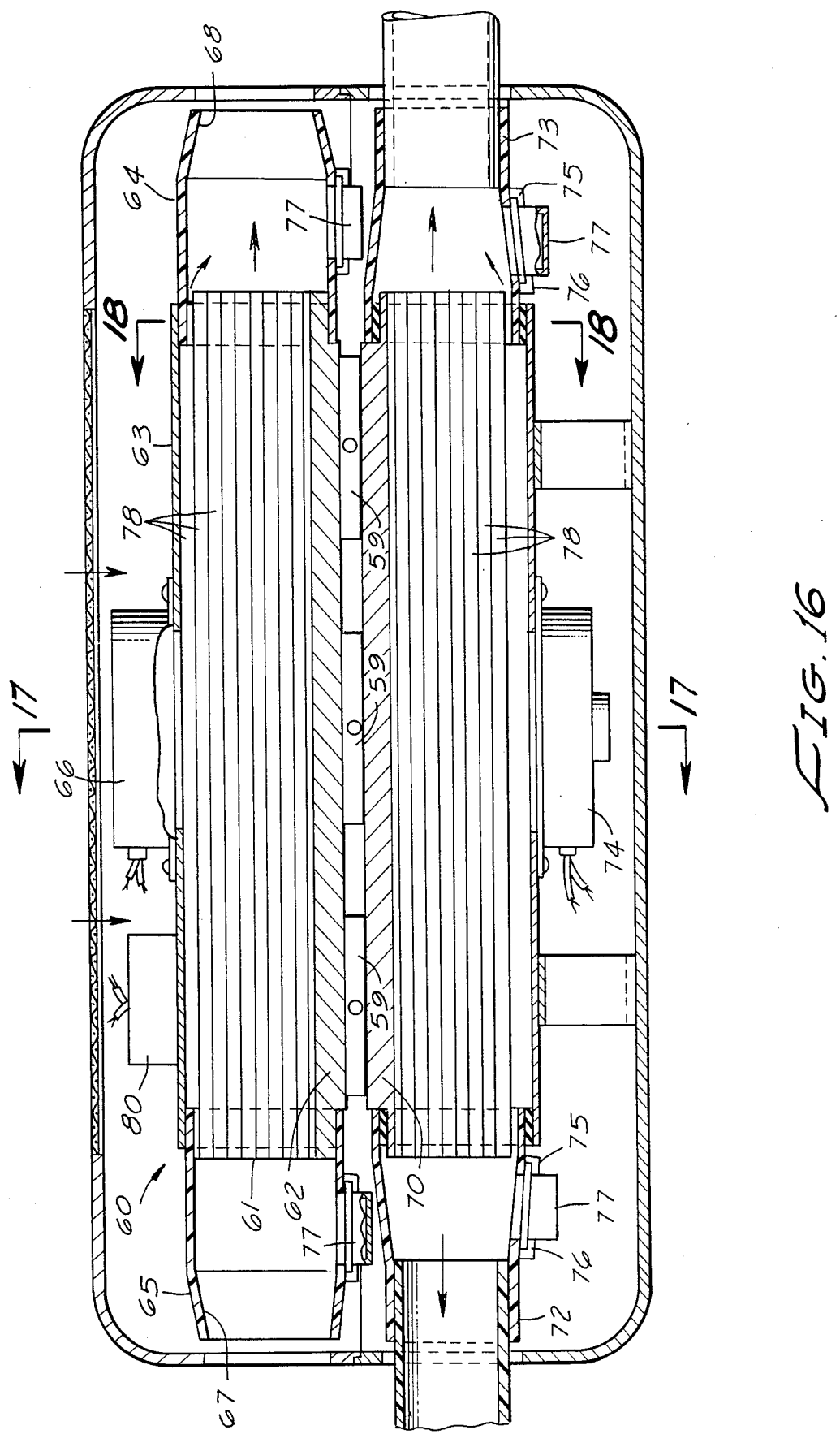

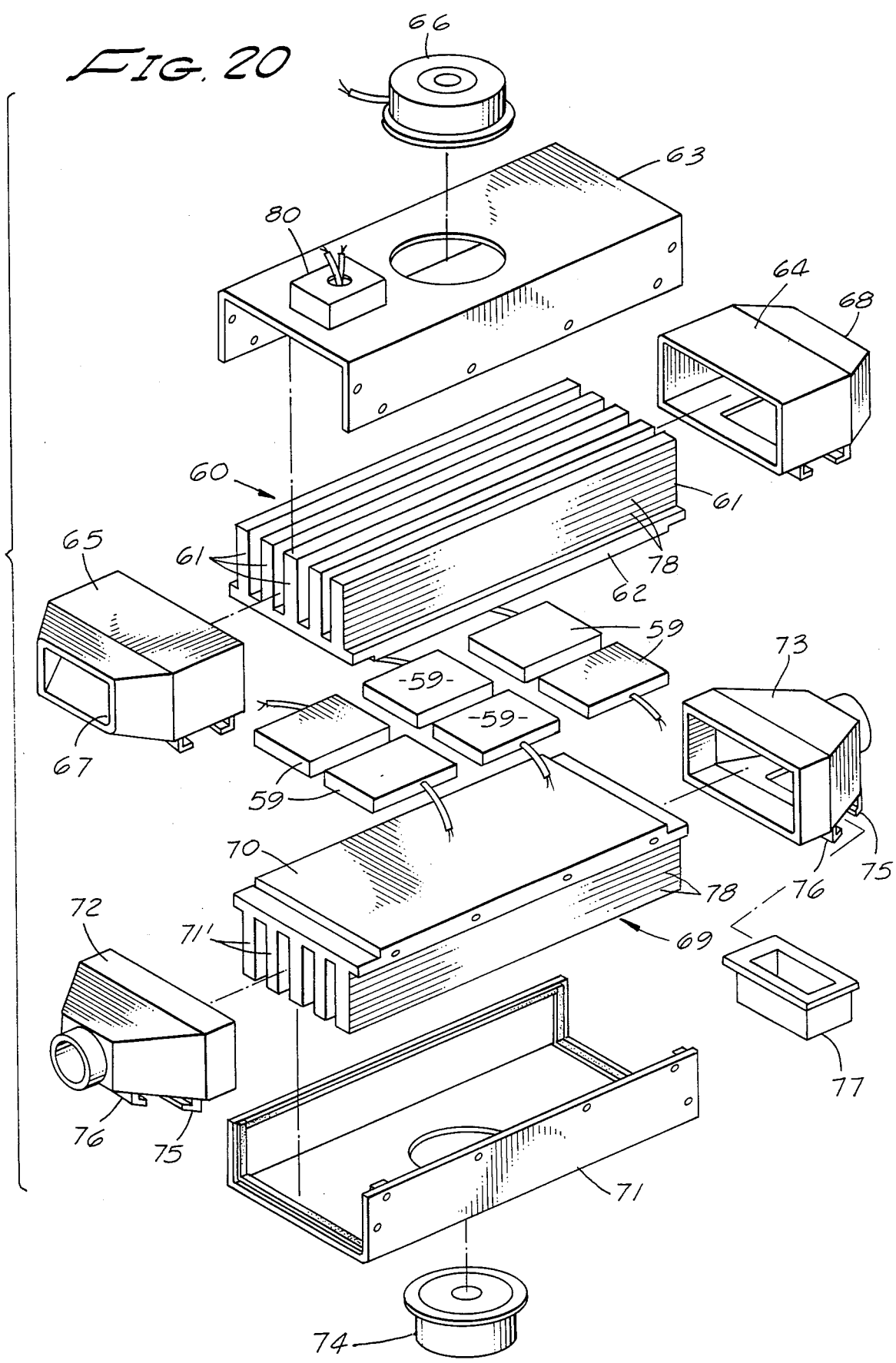

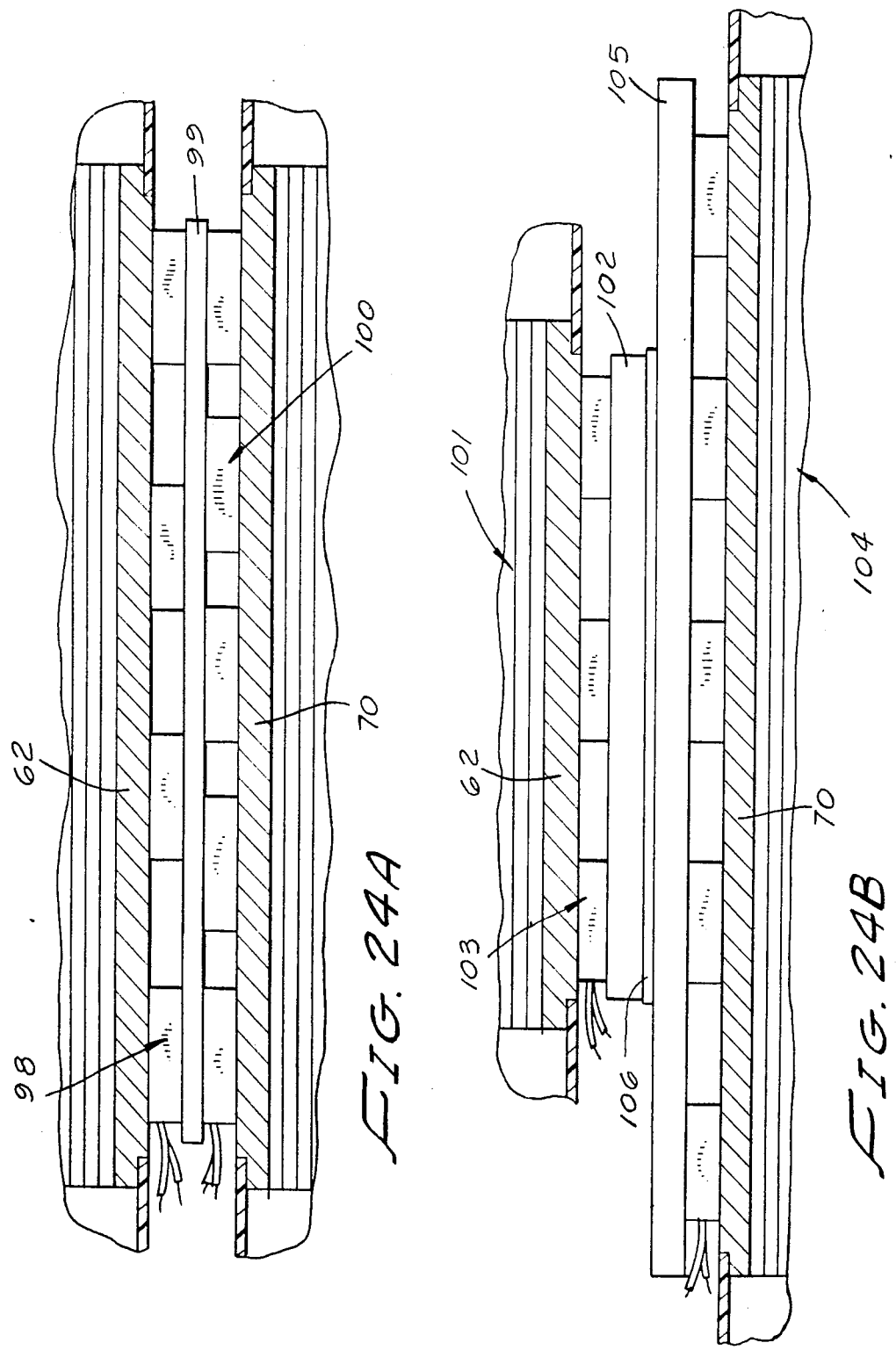

BLANKET ASSEMBLY AND SELECTIVELY ADJUSTABLE APPARATUS FOR PROVIDING HEATED OR COOLED AIR THERETO

The present invention pertains generally to a blanket assembly and apparatus selectively adjustable to provide cooled or heated air to the blanket assembly, as desired.

BACKGROUND OF THE INVENTION

The subject of conditioning air for increasing the comfort of human beings has been the subject of intense study for many years from which it has been learned that for optimal results attention must be paid to a number of factors other than merely heating or cooling the air.

For example, in *The Handbook of Engineering Fundamentals,* John Wiley & Sons, Third Edition 1975, air conditioning is defined broadly as the simultaneous control of temperature, humidity, motion, and purity of air to meet the requirements of human comfort. Some of the principal factors affecting human comfort and welfare as influenced by air environment are the (1) air dry-bulb temperature, (2) humidity, (3) motion, (4) distribution, (5) dust control, (6) bacteria content, and (7) odors. Other factors which may influence comfort, but the effects of which are not so well established at the present time, are (8) light, (9) ozone content, (10) ionic content, and (11) pressure. Human occupancy of a confined space produces a number of important alterations in the properties of the air: (1) oxygen content is decreased slightly; (2) carbon dioxide content is increased slightly; (3) products of decomposition, usually accompanied by odors, are given off; (4) air temperature is raised; (5) humidity is increased by evaporation of moisture from the skin and the lungs; and (6) the number of positive and negative ions in a unit volume of the air is decreased. Also, it has been found that in an occupied space, at least 10 cubic feet of fresh air per minute per person should be provided to adequately remove body heat, body odors, and products of respiration.

Still further, the *American Society of Heating and Ventilation Engineers* provides that the relative humidity shall not be less than 30 percent, nor more than 60 percent, and that the effective temperature shall range between 64° and 69° Fahrenheit when cooling or dehumidification is required.

OBJECTS AND SUMMARY OF THE DISCLOSURE

It is a primary aim and object of the present invention to provide a blanket assembly interconnected with apparatus that is selectively adjustable to provide a supply of either cooled or heated air, as desired.

Another object is the provision of blanket assembly for directing a large number of low velocity and pressure micro-streams of temperature modified air onto an individual covered by the blanket.

Yet another object of the invention is the provision of interconnection means for distributing a portion of the temperature modified air to pillows to be used in conjunction with the blanket assembly.

A still further object is the provision of a blanket assembly and air modifying apparatus as in the above objects in which the humidity of the modified air is controlled and a pleasant scent is added to the air.

In accordance with the disclosure herein, a first version of blanket assembly is provided having an outer layer constructed of a relatively close weave fabric preventing air flow therethrough and which is of suitable geometry and dimensions for use in covering a bed top, for example. Underneath the top layer is a second layer of material edge connected to the top layer and which is constructed of a material permeable to air, such as relatively thin taffeta, for example. A cavity or pocket is formed between the two layers which, in a way to be described, receives pressurized cooled or heated air that passes through the air permeable layer to cool or heat, as the case may be, the individual using the blanket assembly. One end portion of the blanket assembly has an inlet nozzle which can be formed directly from the materials composing a blanket assembly layer, for example, or may include a fitting suitably secured within an opening to the blanket assembly cavity or chamber.

A modified blanket assembly construction includes rigid edge wall members holding the outer and inner layers separated at a predetermined spacing which reduces the possibility of "pinch-off" between the layers restricting air flow within parts of the cavity or chamber.

The apparatus for conditioning air to either a cooled or heated state includes a first heat exchanger consisting of a finned heat exchanging element enclosed within a manifold, which manifold has entrance and exit openings. A second heat exchanger of substantially the same construction as the first is arranged closely adjacent the first heat exchanger. A surface of each exchanger is brought into contact with a plurality of semiconductor plates or elements which upon selective energization warm or cool one of the exchanger surfaces while effecting the opposite to the other exchanger surface. More particularly, electric power interconnected with the thermoelectric plates passes D.C. current through the plates in either of two different directions, one direction effecting cooling and the other producing heating. First and second air impellers are mounted in the heat exchanger manifolds to provide a continuous flow of air therethrough. A flexible hose has one end interconnected with the second heat exchanger and the other with the air inlet to the blanket assembly. A removable condensate collection pan or trap is provided adjacent each exit opening of the second heat exchanger.

In operation, the air impellers are actuated, and electric power is applied to the thermoelectric modules which in accordance with a principle known as the Peltier effect serves to pump heat from one junction for absorption at another junction. Assuming that the ambient temperature is cooler than desired and, therefore, heat is desired in the blanket, the first heat exchanger will be the reference junction for the thermoelectric modules and with electric current passed through the semiconductor plates in the proper direction, heat absorbed at this junction is pumped to the second heat exchanger at a rate proportional to the electric current. The air passing through the second heat exchanger is heated and then pumped to the blanket assembly. The heated air added to the blanket assembly cavity can only make its way out through the relatively thin and air permeable inner layer where it is played upon the body of an individual wrapped in the blanket in low pressure, slow moving micro-streams as well as by direct conduction through the second layer.

Alternatively, when the ambient temperature is warmer than desired, and, therefore, cooling is called for, the electrical supply is switched and now heat absorbed at the second heat exchanger at a rate proportional to the electric current passing through the modules thereby effecting cooling of the air passing through the second heat exchanger. As before, pressurized cool air is passed to the blanket assembly cavity.

Optionally, the apparatus can include a filter to remove dirt and dust, a humidifier (e.g., ultrasonic humidifier), and equipment for ionizing and adding a pleasant scent to the modified air.

DESCRIPTION OF THE DRAWING

FIG. 3 is a perspective, partially fragmentary view of one form of temperature conditioned blanket.

FIG. 4 is a sectional view taken along the line 4—4 of FIG. 2.

FIG. 5 is a side elevational, sectional view taken through the blanket 90-degrees to that of FIG. 4 along line 5—5 of FIG. 2.

FIG. 6 is a sectional view along line 6—6 of FIG. 5.

FIG. 7 is a further sectional view taken along the line 7—7 of FIG. 5.

FIG. 16 is a side elevational, sectional view through the air temperature conditioning apparatus taken along line 16—16 of FIG. 2.

FIG. 20 is an exploded view of the various parts of the apparatus of FIG. 19.

FIGS. 24A and B show two additional forms of cascading Peltier effect elements.

DESCRIPTION OF THE PREFERRED EMBODIMENTS

Figure 1:
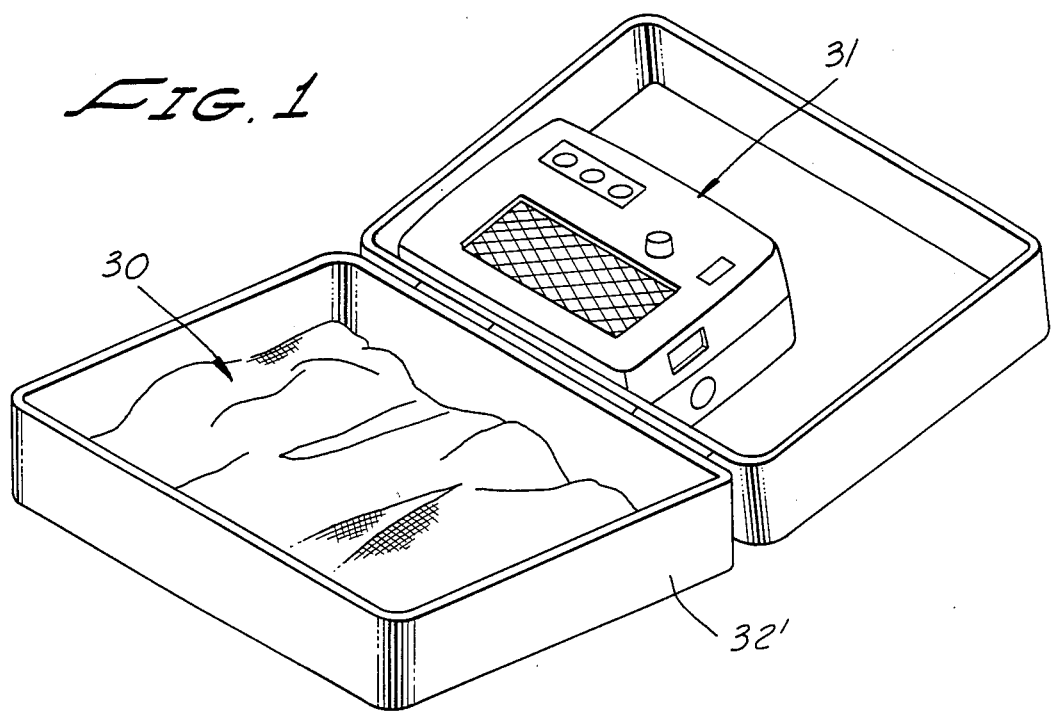
FIG. 1 is a perspective view of a temperature conditioned blanket and conditioning apparatus of the present invention shown stored in a luggage case.
Figure 2:
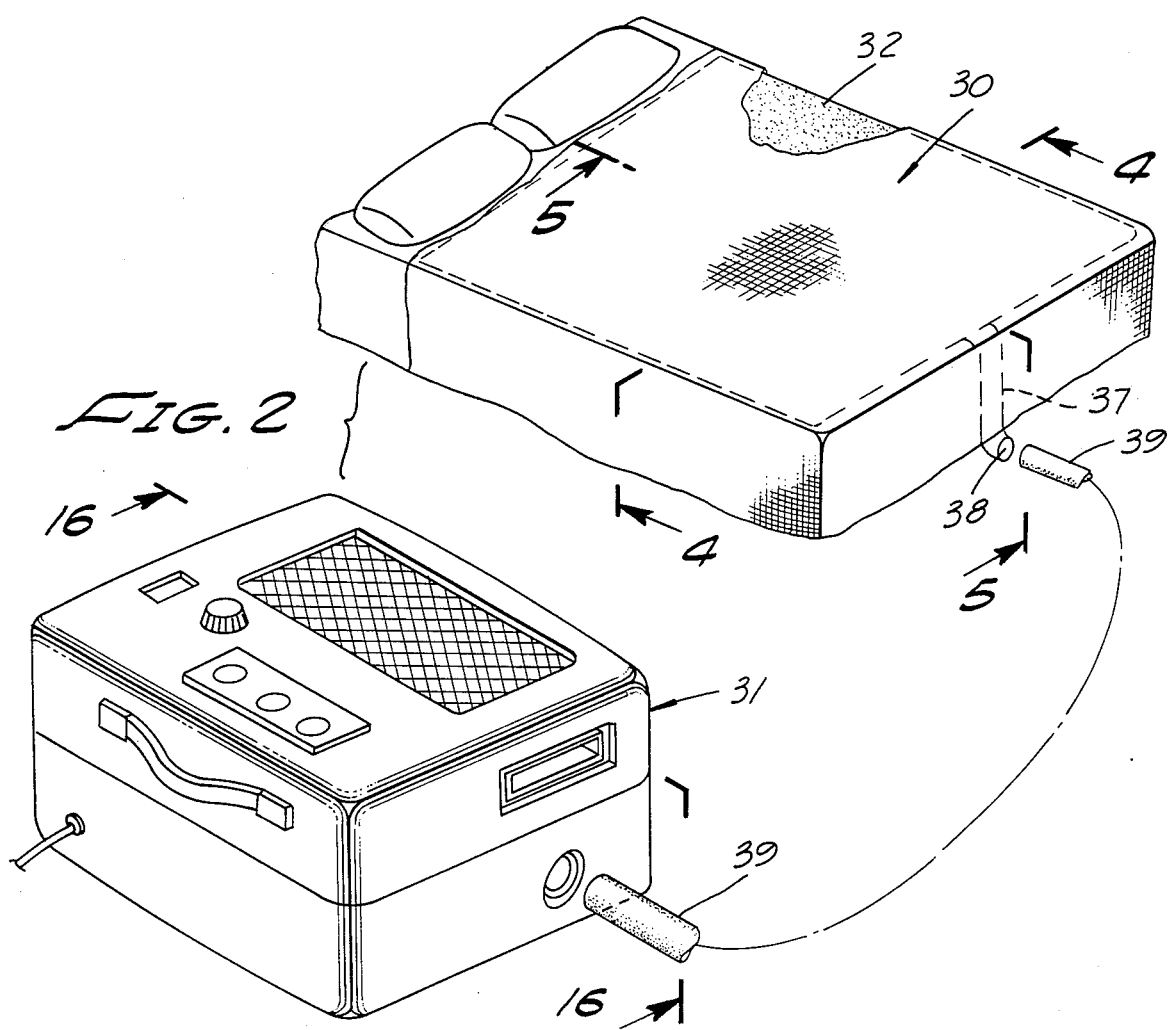
FIG. 2 shows the temperature conditioned blanket in place on a bed and interconnected with the conditioning apparatus adjacent thereto.

With reference now to both FIGS. 1 and 2, a blanket of selectively modifiable temperature is enumerated generally as 30 and, in a way that will be described, is interconnected to air temperature control apparatus 31 which can selectively cool or heat air supplied to the blanket, as desired. That is, a fundamental aspect of the present invention is the provision of a blanket for conventional use on a bed 32, for example, and which in cold weather can be supplied with heated air, or during warm weather with cooled air. When not in use, the apparatus 31 and the blanket 30 may be stored in a luggage case 32' for ready transportation from one location to another during traveling, for example.

With reference now to FIGS. 3 and 4, the blanket 30 is seen to include an outer fabric layer 33 made of a soft pliable fabric material which is closely woven so as to prevent substantially all transfer of air therethrough, or, preferably, the layer may be made of latex. The outer layer can also have any of the usual surface adornment features found in conventional blankets or bed covering coverlets, for example, and is of such dimensions as to extend over the main top surface of the bed 32 and, if desired, downwardly at the sides and end of the bed.

Underneath the part of layer 33 that is intended to extend across the bed top surface, there is a second layer or sheet 35 made of an air permeable material. This second layer 35 is edge stitched or sealed to the layer 33 forming an air chamber or cavity 36 between the layers 33 and 35. As noted, the layer 35 is made of a material that readily allows air to move therethrough such as, for example, taffeta, such that the user of the blanket will be warmed or cooled, as the case may be, by pressurized temperature modified air applied to the chamber 36.

As can be seen best in FIG. 3, the layers 33 and 35 are edge stitched or sealed in a suitable manner around substantially the entire periphery except for a short portion at the front or leading edge of the blanket as it lies on the bed. At the front edge a portion of the air impervious layer 33 is bent onto itself forming a hollow tube or nozzle 37 with an open end 38 that is in direct communication with the chamber 36.

In use of the blanket as described to this point, the blanket 30 is located on the bed or wrapped about the individual. A flexible tube or hose 39 has one end interconnected with the air temperature controlling apparatus 31 and its other end received within nozzle opening 38. Since the edges of the blanket are sealed, pressurized conditioned air entered into the cavity 36 moves outwardly through the air permeable layer 35 to be directed onto the individual over a relatively large surface and through a very large number of small pores in the layer 35.

The inlet nozzle 37 for the blanket 30 may be relatively short so as to really only extend partway down the end of the bed and be covered by the bedspread, or it may be longer extending to the floor, as shown in FIG. 5, for example.

Figure 9:
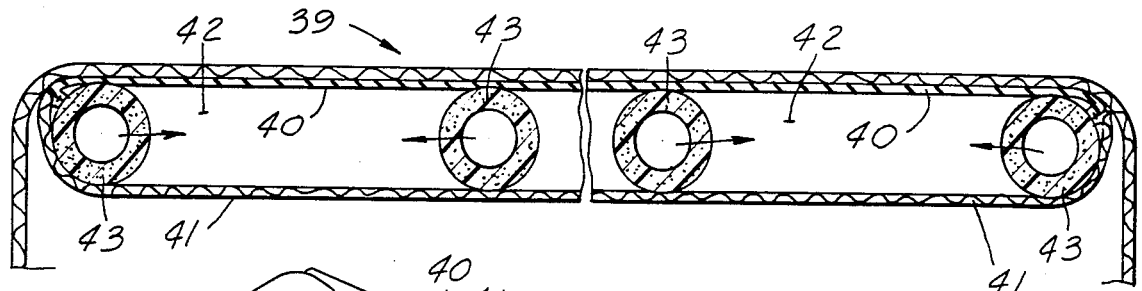
FIG. 9 is a sectional view through the blanket of FIG. 8 taken along line 9—9.
Figure 8:
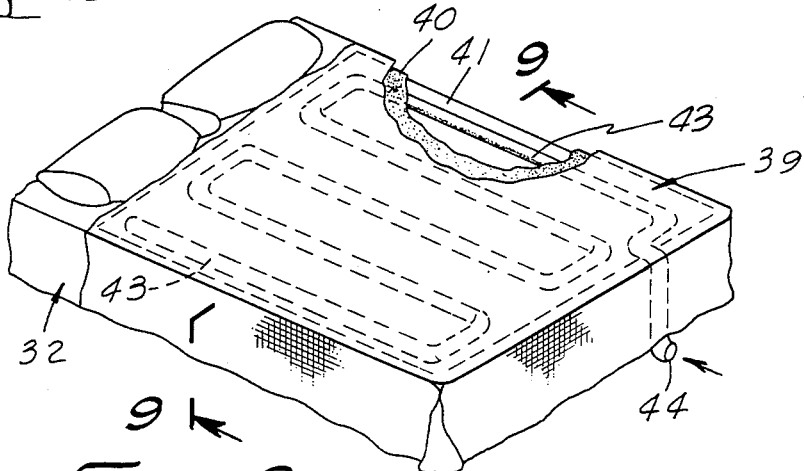
FIG. 8 is a perspective, partially fragmentary view of an alternate form of temperature conditioned blanket.

FIGS. 8 and 9 depict a further form of blanket 39 for use with the apparatus 31. As in the first described blanket it includes an outer air impervious layer 40 and an inner air-permeable layer 41 which are edge stitched or sealed to form an intervening chamber or cavity 42. Additionally, a length of flexible tubing 43 formed from a porous material is located within the cavity 42 and has one end affixed to an air inlet nozzle 44 and its other end sealed off. The tubing 43 is arranged into a sinuous path so as to extend over substantially the full horizontal region of the blanket. Pressurized conditioned air moves into the flexible tubing 43, outwardly through the tubing pores and then through layer 41 to warm or cool the user, as the case may be.

Figure 10:
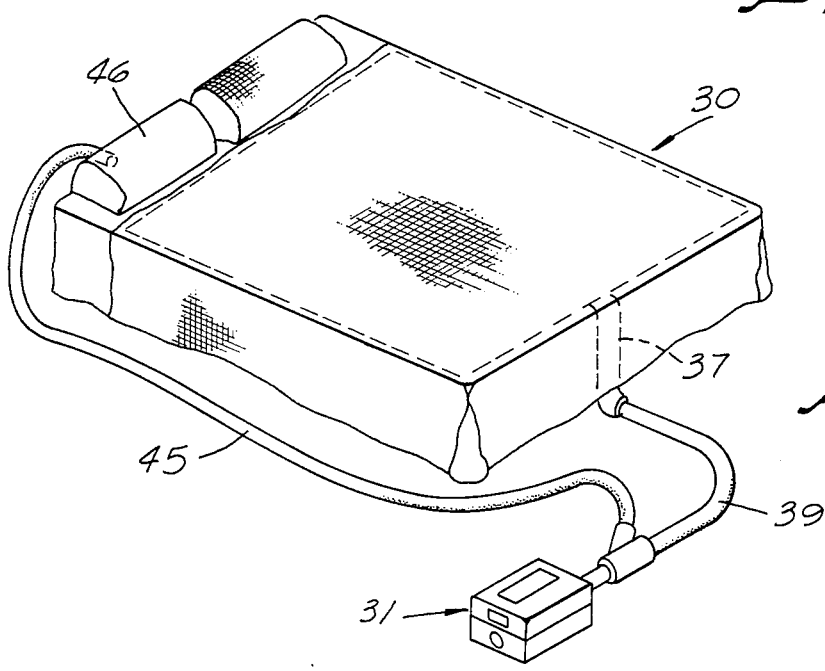
FIG. 10 is a still further embodiment of the invention showing the blanket with a temperature conditioned pillow.

FIG. 10 depicts yet another embodiment in which another conditioned air hose 45 interconnects with the primary air hose from the apparatus 31 to provide conditioned air to a bed pillow 46. In this way, conditioned air is made available to the neck and shoulders of an individual resting or sleeping in the bed as well as being directed onto the trunk and extremities as already described.

Figure 11:
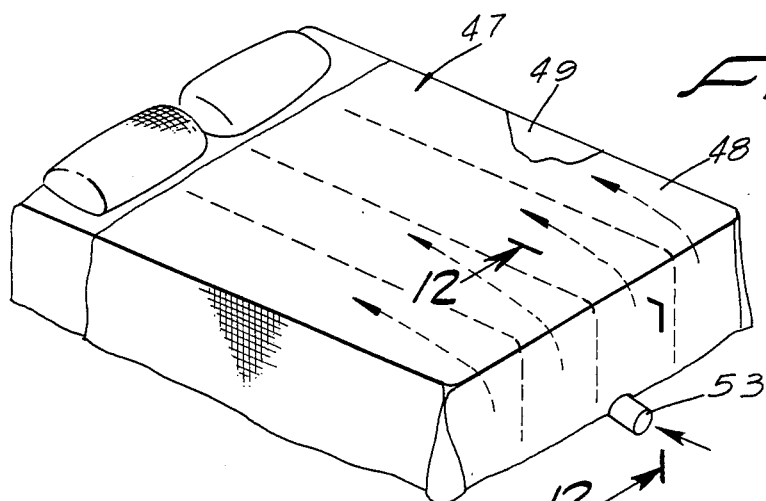
FIG. 11 is a still further embodiment of temperature conditioned blanket.
Figure 12:
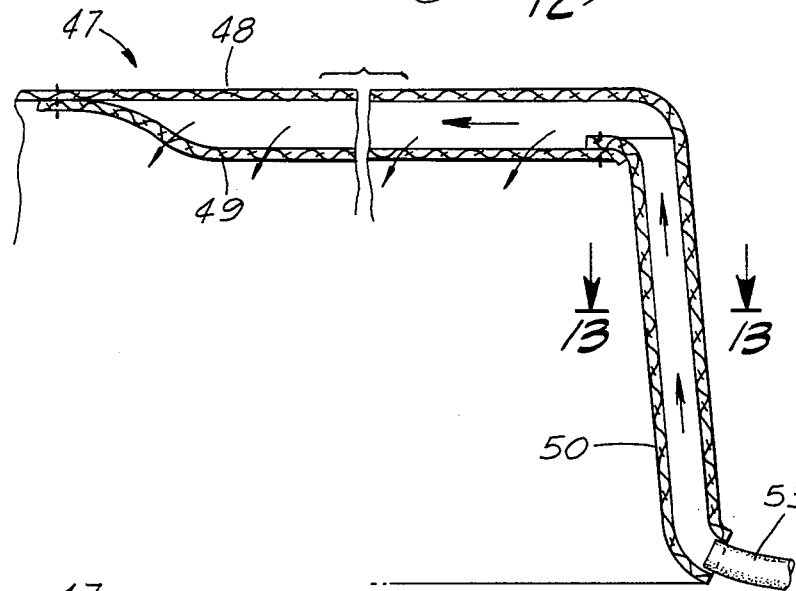
FIG. 12 is a sectional view taken along line 12—12 of FIG. 11.
Figure 13:
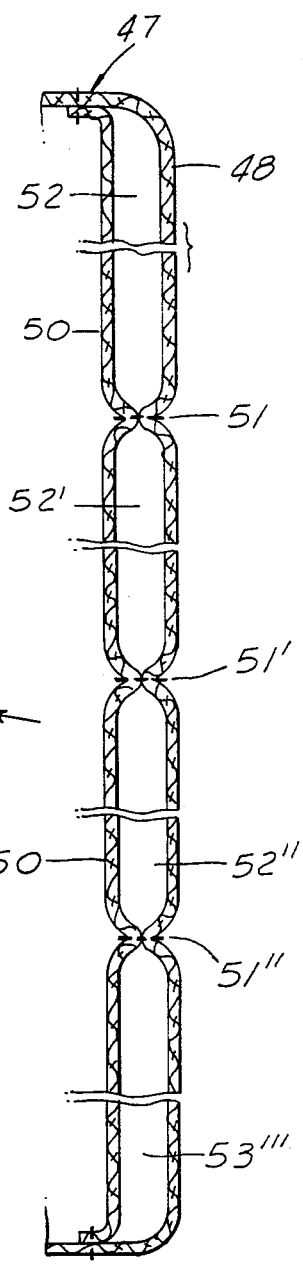
FIG. 13 is a sectional view taken along line 12—12 of FIG. 12.
Figure 14:
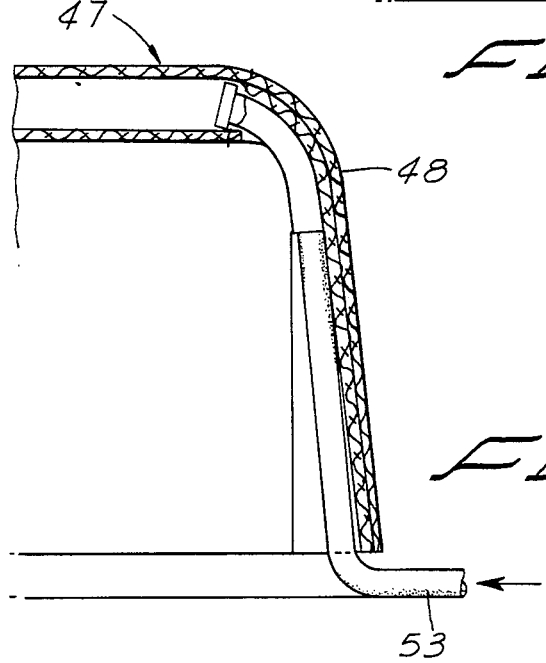
FIG. 14 is a side elevational, sectional view of a further embodiment.

A still further version of blanket for use with the apparatus 31 is shown in FIGS. 11 through 13 and enumerated as 47. In this embodiment the upper air impervious layer 48 not only covers the entire upper surface of the bed but has a further portion extending down the front of the bed substantially to floor level (FIG. 12). The underlying air permeable layer 49 is edge stitched or otherwise sealed to layer 48 and has a geometry and dimensions sufficient to cover only substantially the upper surface of the bed. An air impervious section 50 is sealed or stitched to layer 49 along the upper front edge of the bed and extends downwardly to the floor level. In addition, a plurality of longitudinal stitch or sealing lines 51, 51'—are provided between the layers 48 and 49, and between the layer 48 and section 50 as is shown in FIG. 13. These sealing lines serve to form a plurality of longitudinally extending chambers 52, 52'—from just short of the floor level in the front of the bed all the way to the opposite extremity of the blanket. As before, an inlet nozzle 53 receives an end of the flexible tubing interconnected with the air conditioning apparatus. In use, the pressurized conditioned air moves from the inlet nozzle into plurality of the blanket chambers 52, 52'—of which establishes a superior and highly uniform distribution of conditioned air.

Figure 15:
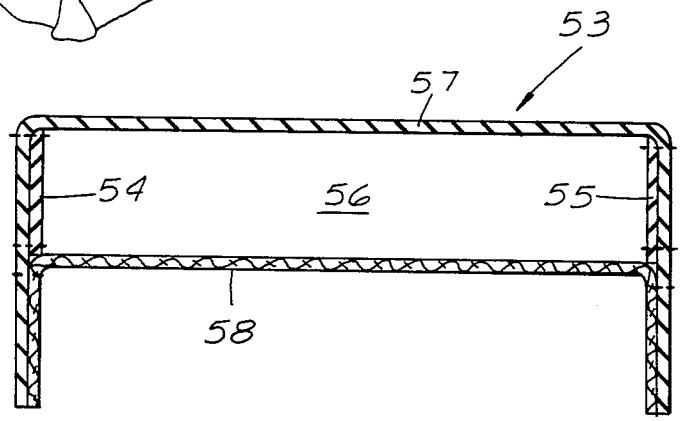
FIG. 15 is a side elevational, sectional view of a still further blanket embodiment.

FIG. 15 shows a still further form of blanket or cover 53 which offers increased uniformity of modified air transfer in that pinch-off of the air chamber between the blanket layers is prevented or substantially reduced. Comparing with the FIG. 4 embodiment, it is to be noted that a pair of wall members 54 and 55 are formed at each side of the air chamber 56 by incorporating extra blanket material into those regions. The permeable inner layer 58 is secured to the outer layer at points below the lower edge of the wall members 54 and 55. In use, even though a user's body will cause the inner layer to bulge upwardly toward the blanket outer layer, the wall members maintain a substantial space for the chamber 56 avoiding pinch-off.

For the ensuing description of the air temperature modification or conditioning apparatus 31, reference is now made to FIG. 20 where its various parts are shown in exploded relation. The essential temperature modification means consists of a plurality (e.g., three) of heating/cooling semiconductor plate elements 59 which, in a way that will be described, have their temperature increased or decreased, as desired, depending upon the manner of electrical energization. More particularly, such elements consist of a quantity of bismuth telluride heavily doped to produce either an N or P type semiconductor. These semiconductor elements are located in contact with two air transfer means, one in contact with ambient air outside the blanket and another of which contacts air to be modified and pumped into the blanket chamber/s. It can be shown that, heat absorbed at a "cold" junction of the semiconductor elements is pumped to the "hot" junction at a rate proportional to the electric current passing through the elements, with the direction of heat flow being determined by the polarity of energizing current. Such elements are commercially available under the trade designation 950-71 from Thermoelectric Cooling of America, Chicago, Ill.

A first heat exchanger 60 is preferably a metal (e.g., copper) extrusion, stamping or forging, having a plurality of upstanding, spaced apart plates or fins 61 on one surface and the opposite surface 62 being relatively flat for contacting engagement with conductor elements 59 during assembly. The first heat exchanger 60 finned side is enclosed within a manifold housing 63 with two end caps 64 and 65 enclosing the housing ends. A fan 66 is fixedly secured in the upper wall of the housing such that it will take air from the surrounding or ambient environment and pump it into the manifold across the fins or plates of the exchanger where heat is exchanged in accordance with known physical laws and then pumped out through end cap openings 67 and 68 back in the environment.

A second heat exchanger 69, which is larger than the first described heat exchanger, has its flat surface 70 brought into abutting contact with the opposite major surfaces of semiconductor plates or elements 59. A manifold housing 71 is received over the exchanger fins 71' or plates and the ends are enclosed by end caps 72 and 73 having nozzle-like openings which can receive the end of a flexible hose for a purpose to be described. The outer housing wall has an opening within which is received a further fan or air impeller 74 which in one mode of use draws air from the outside inwardly to the manifold and across the heat exchanging surfaces of the fins and outwardly through a flexible tube received in an end cap opening to the blanket assembly. The remaining end cap opening is closed off to increase air flow.

Exchanger 69, E2, has a smaller $\Delta t$ (i.e.) temperature differential) than E1 because it is larger and has more air passing through it. For optimum Peltier performance, the total $\Delta t$ between the "cold" side and the "hot" side of an element should be held to a minimum. Since E1 is on the working side, it is desirable to have as much of the $\Delta t$ as possible occur on this side. In explanation, there is only a given amount of t available for a given power setting of the apparatus, and by the described construction the t for E2 (the non-working side) is kept as low as possible.

The lower walls of end caps 72 and 73 are open, and spaced apart guide rails 75 and 76 extending transversely of the caps and defining the lower opening of each. An open-top condensate pan or trap 77 has outwardly extending flanges of such dimensions as to enable sliding receipt on the guide rails. The pans receive condensate during use and are readily removable to dispose of the collected condensate as needed. These pans are only needed on the heat exchange delivering modified air, since the reference heat exchanger air experiences a much smaller temperature variation and will, accordingly, produce much less moisture.

Figure 17:
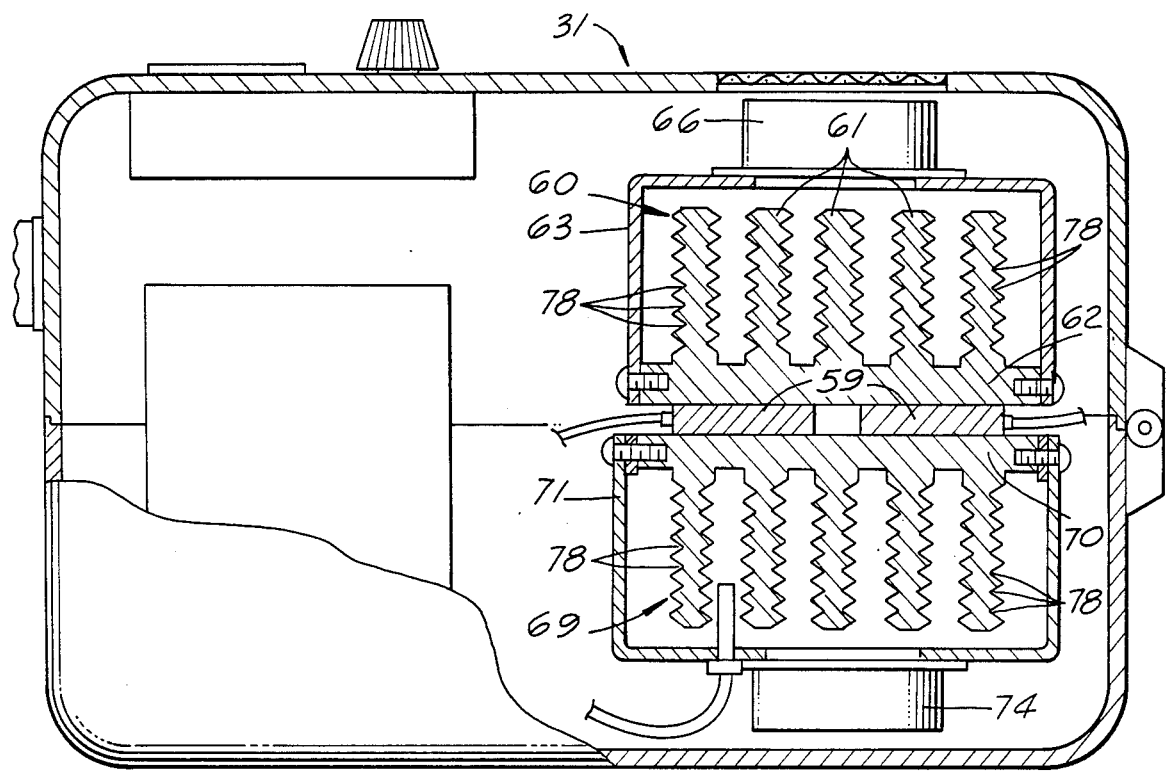
FIG. 17 is a further sectional view taken along line 17—17 of FIG. 16.
Figure 18:
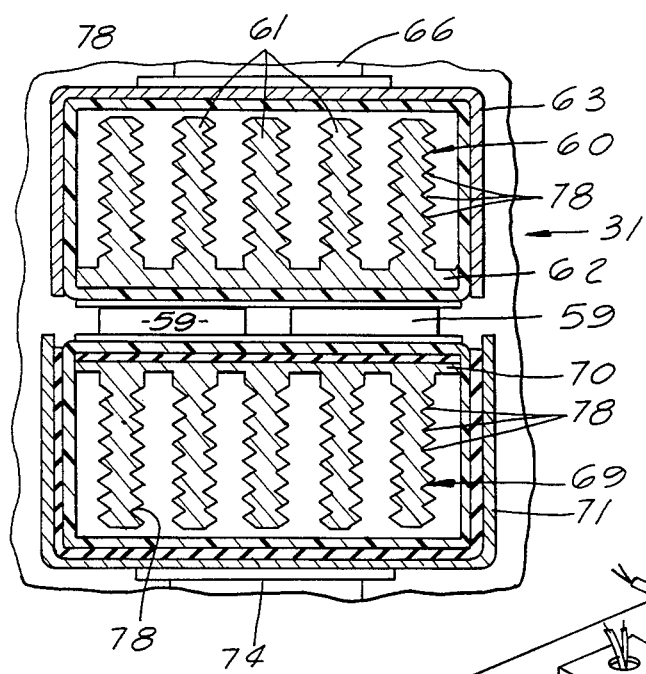
FIG. 18 is yet another sectional view taken along the line 18—18 of FIG. 16.
Figure 19:
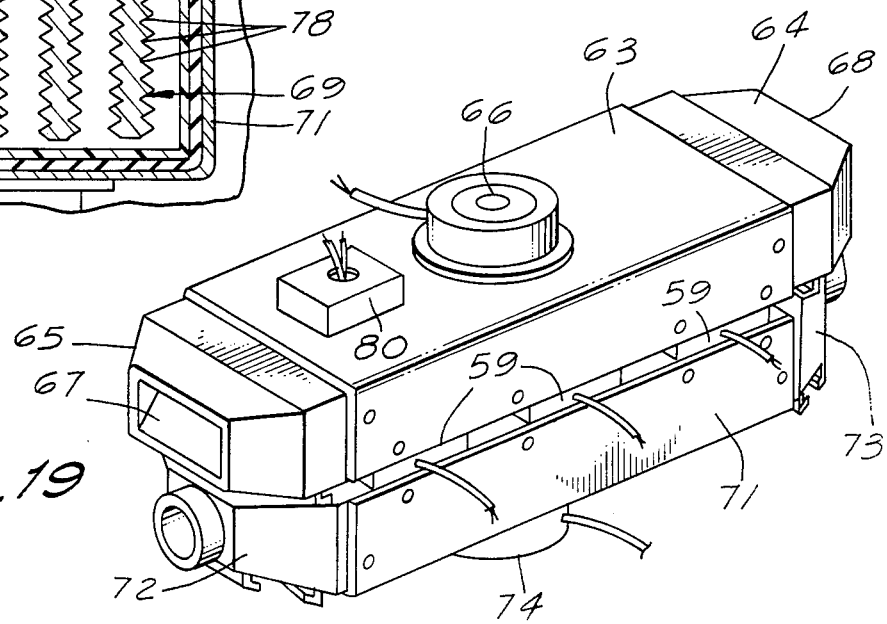
FIG. 19 is a perspective view of the temperature conditioning apparatus.

FIGS. 16 and 19 show the air temperature modification apparatus parts of FIG. 20 in assembled unitary relation. Also, FIGS. 16, 17 and 18 show the unitary air conditioning apparatus of FIG. 19 mounted within a housing along with other control and electrical energizing apparatus, to be described. It is this entire arrangement that is depicted as the apparatus 31 in FIGS. 1 and 2, for example.

FIGS. 17 and 18 show the detailed surface configuration of the heat exchanger fins or plates 61 as having a plurality of longitudinally extending surface grooves 78. In this manner, the heat exchanging surface of the plates 61 is substantially increased which enhances overall apparatus operational efficiency.

Figure 21A:
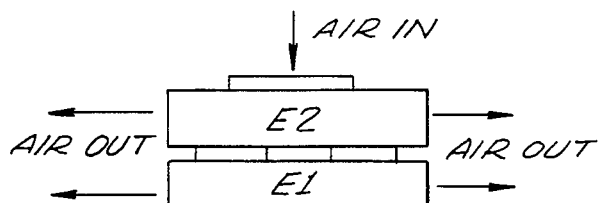
FIGS. 21A, B and C depict, in schematic form, different ways of passing air through the temperature conditioning apparatus.
Figure 21B:
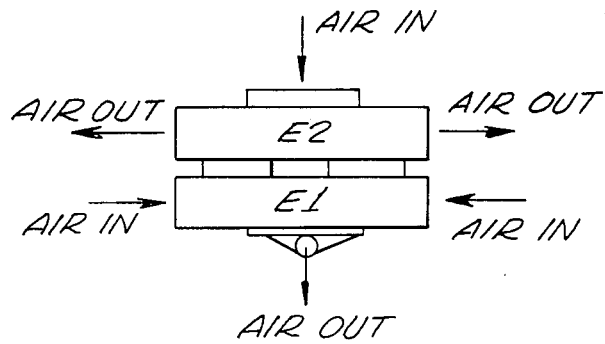
Figure 21C:
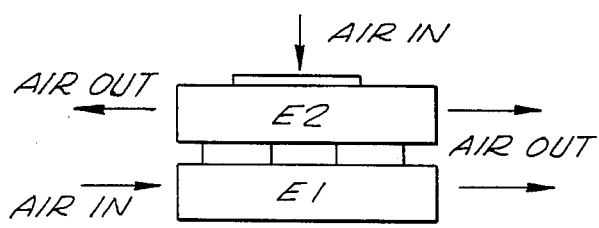

For the ensuing discussion of various ways to pass air through the apparatus for achieving cooled or heated air, reference is made to FIGS. 21A, 21B, and 21C. FIG. 21A shows the manner of passing air through the first and second heat exchangers as it has been described to this stage, namely, the air is forced into both manifolds by the fans centrally located in the respective manifold housings and air exits through one or both of the openings in the end caps.

FIG. 21B shows an alternate form of air passage through the heat exchangers in which one of the heat exchangers, E2, is operated in the same way as in 21A. However, in the second exchanger the fan instead of pumping air into the manifold pumps it out drawing air into each of the end cap openings.

FIG. 21C is a still further embodiment in which an air impeller may be located in either end cap opening of the exchanger E1 and there is no central manifold housing opening. Accordingly, air either forced or drawn into the manifold passes across the exchanger fins and out the other end cap. The heat exchanger E2 is the same as in FIGS. 21A and 21B.

Figure 22:
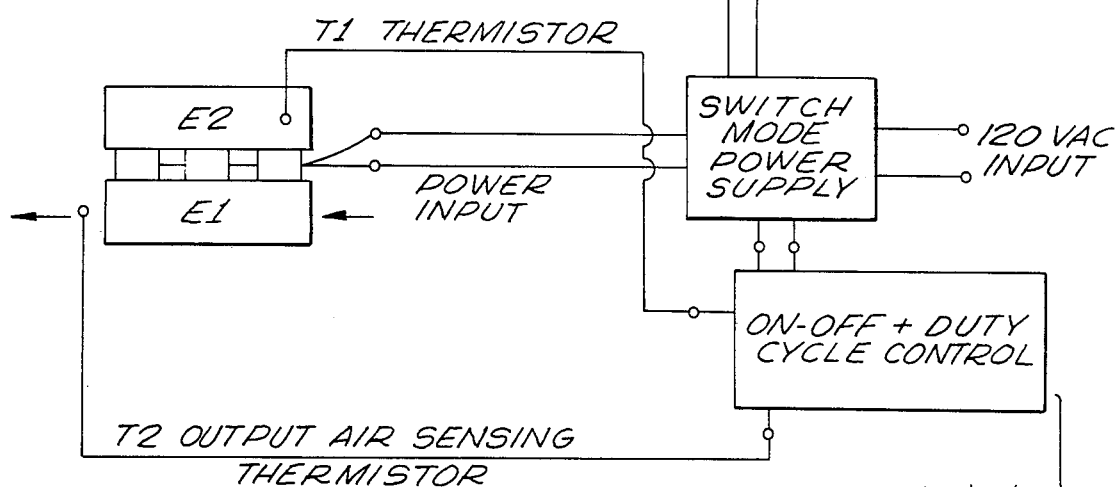
FIG. 22 is a function block schematic of the electrical control and power supply for the air temperature conditioning apparatus.

A function block circuit schematic of the electrical control and energization for the semiconductor elements 59 to either heat or cool air is depicted in FIG. 22. The block identified as E2 is the heat exchanger through which ambient air is passed and serves as a reference temperature for the apparatus. A thermistor T1, which is a well-known device having electrical resistance functionally related to its temperature, is located within the E2 manifold and has leads interconnected within the block identified as On-Off and Duty Cycle Control providing an electric reference signal representative of the ambient air temperature. E1 is the heat exchanger for modifying or conditioning the air and includes a further thermistor T2, the output thermistor, for measuring the temperature of the air after it has been conditioned. A Switch Mode Power Supply is under the control of the On-Off and Duty Cycle Control which determines when and how long the power is to be applied to the semiconductor elements, and, more particularly, the direction of the current flow through the elements in order to either cool or heat the air passing through heat exchanger E1.

An optional control identified generally as Infra-Red Remote Control is actuated by pushbuttons to increase or decrease the heating or cooling of the apparatus and accomplishes by sending out an infrared signal which is picked up by a detector located at the apparatus 31 and, which, in turn, through appropriate circuit logic interconnects and energizes the Switch Mode Power Supply to operate the apparatus as commanded.

Figure 23:
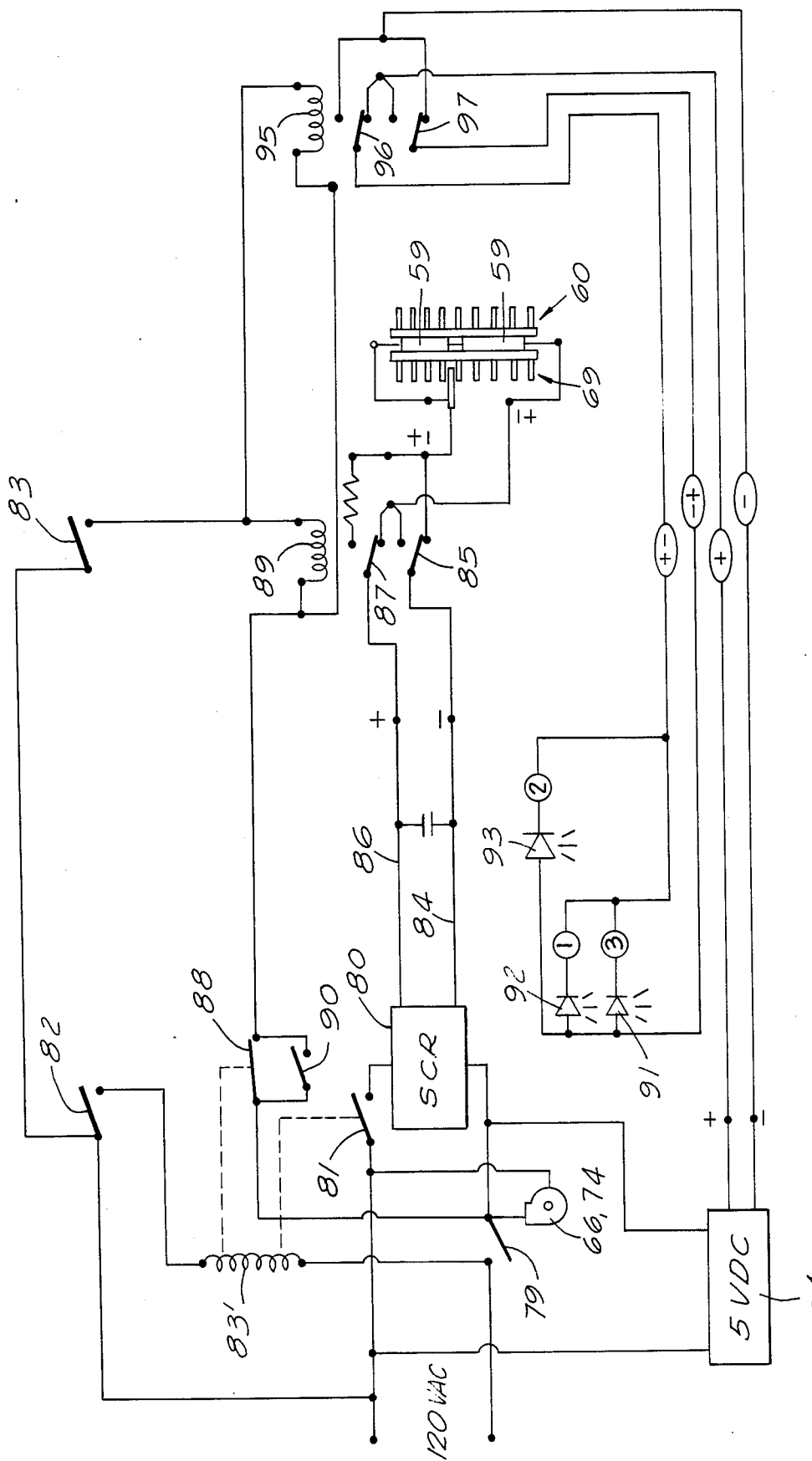
FIG. 23 is a detailed circuit schematic of the electrical control and power supply apparatus of FIG. 21.

A detailed circuit schematic of a preferred form of power and energization control for the apparatus 31 is shown in FIG. 23. A manually operated On-Off switch 79 when switched to On applies line power to the motor drive for the fans 66, 74. This switch as well as all other manual switches of the momentary contact type.

One side of the domestic A.C. power is now available through switch 79 (now closed) to one input terminal of a silicon controlled rectifier (SCR) 80. The other side of the A.C. power is applied to the SCR through normally-open relay point 81 which is closed when power switch 82 is closed energizing relay coil 83'. This relay as well as the others are all latching relays. The SCR on being energized provides a D.C. voltage of appropriate voltage to drive the semiconductor plates 59 for cooling/heating as already described. A full-wave SCR bridge suitable for present purpose is manufactured by Dart Controls of Zionsville, Ind. and sold under the trade designation 250B.

Assuming mode switch 83 is open, a first D.C. line 84 interconnects one output terminal of the SCR through a N/C relay point 85 to one side of semiconductor plates 59, while a second D.C. line 86 passes through a further N/C relay point 87 to energize the other side of semiconductor plates. The semiconductors are now operating in one mode, say, heating.

It is to be noted that when the SCR is connected to provide D.C. power to the semiconductor plates N/C relay point 88 is open preventing energization of mode relay coil 89. The purpose of this is to protect the SCR which could be damaged if its output side were switched (e.g., mode changed) while delivering power. Accordingly, if it is desired to effect a mode switch, first the power switch 82 must be opened taking power off the SCR and closing relay point 88. Now, on closing mode switch 83 coil 89 can be picked up which transfers relay points 85 and 87 to reverse D.C. polarity connection with the SCR. Power switch 82 may now be closed causing the SCR to once again apply power to the semiconductor plates 59, although now in a polarity to effect cooling. N/O relay points 90 are closed when mode relay coil 89 is energized and keep the relay coil energized when power is on the SCR (i.e. when 88 opens).

Light emitting diodes 91–93 (LED) are interconnected with a low D.C. voltage source 94 (e.g., 5 VDC) which is energized when fan switch 79 is closed. At this time D.C. power is applied to the LED's in such polarity as provide a certain color light (e.g., red) which identifies, say, that the apparatus is in "heating" mode.

Simultaneously with mode switch 83 closing, relay coil 95 is energized transferring points 96 and 97 which reverses polarity of the D.C. voltage applied to LED's 91–93. Polarity reversal produces a different color of illumination by the LED's (e.g., green) signifying that the apparatus is now in the "cooling" mode.

The silicon controlled rectifier 80 is heat sensitive and, therefore, should be located within the apparatus 31 in a manner not exposing it to excessive heat from the semiconductor plates 59. As shown in FIG. 19 the SCR 80 is mounted directly onto the top surface of the manifold 63 and in good contact therewith such that heat generated by the SCR is at least partly conducted away in the air stream.

In the first described embodiment, the Peltier plates 59 are arranged in a single plane with all of the plates contacting surface 62 of exchanger 60 as a temperature reference and contacting surface 70 of exchanger 69 to modify its temperature. FIGS. 24A and B depict a cascading arrangement of Peltier semiconductor plates that is believed to posses certain advantages in operation over the single plane arrangement. As shown in FIG. 24A a first set of Peltier devices 98 are mounted onto an interface plate 99 and all have a surface contacting heat exchanger surface 62. A second set of Peltier devices 100, which in number exceed the devices 98, are mounted to contact the opposite side of the interface plate as well as exchanger surface 70.

FIG. 24B includes a first module 101 consisting of a base plate 102 with a number of Peltier devices 103 mounted thereon, and a second module 104 consisting of a base plate 105 with a larger number of Peltier devices mounted thereon. The two modules are assembled together by abutting the base plates together and with a thermal grease 106 increasing the thermal contact, or, optionally, providing a solder layer interface. The two so assembled modules are then brought into contact with the heat exchanger surfaces 62 and 70.

By the use of either cascading system of FIGS. 24A or 24B, the total Δt is increased allowing for a smaller exchange E1 for achieving the same cooling or heating power output allowing savings in size, weight and manufacturing cost.

It is contemplated that the described air modifying apparatus can be enhanced by adding known equipment to ionize the conditioned air or to add a pleasant scent to the air. Moreover, under certain circumstances it may be desirable to humidify the conditioned air and could most effectively be accomplished by coupling an ultrasonic humidifier with the conditioned air outlet.

I claim:

1. A blanket for connection with a supply of pressurized temperature-modified air, comprising:
   an outer layer constructed of an air impervious material;
   an inner layer constructed of a material readily permeable by pressurized air, said inner layer being arranged in major surface area contacting relation with the outer layer;
   sealing means interconnecting the outer and inner layers arranged in a substantially continuous closed path leaving an unsealed and separable portion of said outer and inner layers inwardly of the sealing means; and
   inlet means communicating with the unsealed portion between the outer and inner layers for introducing the pressurized temperature-modified air therein at least a part of which pressurized air exits through the inner layer.

2. A blanket as in claim 1, in which the outer layer is constructed of latex.

3. A blanket as in claim 1, in which the inner layer is constructed of taffeta.

4. A blanket as in claim 1, in which the inlet means is integral with the outer layer and formed into a tubular member.

5. A blanket as in claim 1, in which the sealing means includes a continuous line of stitching.

6. A blanket as in claim 1, in which a plurality of additional sealing means located inwardly of the first recited sealing means interconnect the outer and inner layers forming a number of individual cavities between said layers, each individual cavity being in communication with the inlet means.

7. A blanket as in claim 1, in which there is further provided a flexible hollow tube with porous walls located between the blanket outer and inner layers, said tube having one end connected to the inlet means and the opposite end sealed off.

8. A blanket as in claim 7, in which the tube is arranged into a sinuous configuration.

9. A blanket as in claim 1, in which rigid wall members are located between the layers holding the outer and inner layers in spaced apart relation.

10. A blanket as in claim 9, in which the outer layer is constructed of latex.

11. A blanket as in claim 9, in which the inner layer is constructed of taffeta.

12. A blanket as in claim 9, in which the inlet means is integral with the outer layer and formed into a tubular member.

13. A blanket as in claim 9, in which the sealing means includes a continuous line of stitching.

14. A blanket as in claim 1, in which the pressurized temperature-modified air is provided by apparatus including,
   a first heat exchanger having a flat surface and means for moving ambient air across the exchanger to establish the flat surface at a reference temperature;
   a second heat exchanger having a flat surface and means for moving air across the exchanger;
   at least one Peltier plate in contact with each of the heat exchanger flat surfaces; and
   a selectively controllable D.C. power source interconnected with said Peltier plate.

15. A blanket as in claim 14, in which the selectively controllable D.C. power source includes means for reversing polarity of D.C. power applied to the Peltier plate.

16. Apparatus externally located to a blanket for providing pressurized, temperature modified air to an air impermeable outer layer separated from an air permeable inner layer, comprising:
   a first heat exchanger with a heat exchanging surface;
   a first air impeller mounted to pass ambient air through the first heat exchanger;
   a second heat exchanger with a heat exchanging surface;
   a second air impeller mounted to pass ambient air through the second heat exchanger;
   a plurality of Peltier effect semiconductor elements arranged to contact the heat exchanging surfaces of said first and second heat exchangers; and
   selectively actuatable D.C. power source means for applying D.C. power to said Peltier effect semiconductor elements of a first polarity to raise the temperature of the second heat exchangers and of a second polarity to lower the temperature of the second heat exchanger.

17. Apparatus as in claim 16, in which a flexible hose has its ends removably connected to the second heat exchanger and the blanket, respectively.

18. Apparatus as in claim 16, in which the first heat exchanger includes a manifold with the first air impeller mounted to the manifold, the heat exchanging surface for said first heat exchanger lying outside the manifold;
   the second heat exchanger includes a second air impeller mounted to said manifold, the heat exchanging surface of the second heat exchanger lying outside the manifold; and
   the Peltier effect semiconductor elements being arranged in a common plane with opposite sides of the elements contacting the respective heat exchanging surfaces.

19. Apparatus as in claim 16, in which the D.C. power source means includes a silicon controlled rectifier mounted to the outside surface of the first heat exchanger manifold in heat conducting relation.

20. Apparatus as in claim 16, in which the Peltier effect semiconductor elements are arranged in two parallel planes and contacting all of the semiconductor elements.

* * * * *